(12) United States Patent
Chikkali et al.

(10) Patent No.: US 12,060,363 B2
(45) Date of Patent: Aug. 13, 2024

(54) ISOHEXIDE-DIOXALATE COMPOUND, ITS POLYMERS AND APPLICATION THEREOF

(71) Applicant: Council of Scientific & Industrial Research, New Delhi (IN)

(72) Inventors: Samir Hujur Chikkali, Pune (IN); Kadhiravan Shanmuganathan, Pune (IN); Bhausaheb Rajput, Pune (IN); Farsa Ram, Pune (IN)

(73) Assignee: COUNCIL OF SCIENTIFIC & INDUSTRIAL RESEARCH, New Delhi (IN)

( * ) Notice: Subject to any disclaimer, the term of this patent is extended or adjusted under 35 U.S.C. 154(b) by 202 days.

(21) Appl. No.: 16/629,862

(22) PCT Filed: Jul. 12, 2018

(86) PCT No.: PCT/IN2018/050457
§ 371 (c)(1),
(2) Date: Jan. 9, 2020

(87) PCT Pub. No.: WO2019/012560
PCT Pub. Date: Jan. 17, 2019

(65) Prior Publication Data
US 2021/0147438 A1 May 20, 2021

(30) Foreign Application Priority Data
Jul. 12, 2017 (IN) .............................. 201711024522

(51) Int. Cl.
*C07D 493/04* (2006.01)
*C08G 63/672* (2006.01)

(52) U.S. Cl.
CPC ......... *C07D 493/04* (2013.01); *C08G 63/672* (2013.01)

(58) Field of Classification Search
CPC ............................ C07D 493/04; C08G 63/672
See application file for complete search history.

(56) References Cited

U.S. PATENT DOCUMENTS

| | | | | |
|---|---|---|---|---|
| 4,208,511 A * | 6/1980 | Shalaby | ........... | A61B 17/06133 528/272 |
| 6,291,629 B1 * | 9/2001 | Kricheldorf | ....... | C08G 63/6856 528/176 |
| 6,737,481 B1 * | 5/2004 | Kurian | .................. | C08L 67/025 524/483 |
| 2003/0204029 A1 * | 10/2003 | Brandenburg | ....... | C08G 63/668 525/444 |
| 2003/0212244 A1 * | 11/2003 | Hayes | .................. | C08G 65/405 528/298 |
| 2010/0160548 A1 * | 6/2010 | Noordover | ............. | C08G 63/82 525/440.15 |
| 2011/0237757 A1 * | 9/2011 | East | ...................... | C08G 63/664 525/437 |
| 2014/0336092 A1 * | 11/2014 | Chen | .................... | C10M 129/76 508/308 |
| 2017/0101504 A1 * | 4/2017 | Ahn | ...................... | C08G 63/672 |

FOREIGN PATENT DOCUMENTS

JP 2006161017 * 6/2006
WO 2005103111 A1 11/2005

OTHER PUBLICATIONS

Wu et al : "Fully Isohexide-Based Polyesters: Synthesis, Characterization, and Structure-Properties Relations", Macromolecules, 2013, 46, pp. 384-394. (Year: 2013).*
Joachim Tlliem et al "Synthesis of Polyterephthalates Derived from Dianhydrohexitols", Polymer Butletin 11, 365-369 (1984) (Year: 1984).*

(Continued)

*Primary Examiner* — Frances Tischler
*Assistant Examiner* — Gennadiy Mesh
(74) *Attorney, Agent, or Firm* — Dinsmore & Shohl LLP

(57) ABSTRACT

Embodiments of this disclosure are directed to isohexide-dioxalates compounds of formula (I), and polymerization processes that utilize diols, oxalic acid, and compounds according to formula (I):

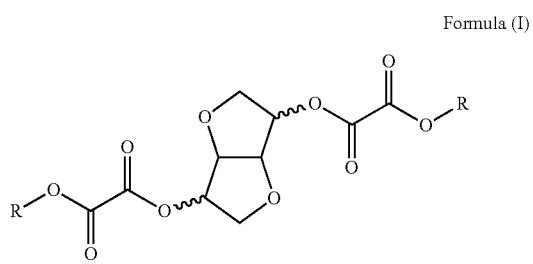

Formula (I)

Embodiments of this disclosure also include polyoxalates compounds of formula (II), polymerization processes for the production of polymers having a general structure according to formula (II):

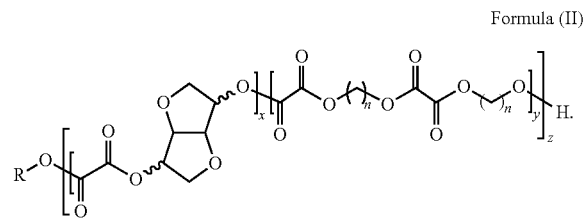

Formula (II)

12 Claims, 6 Drawing Sheets

(56) References Cited

OTHER PUBLICATIONS

Masahiko Okada et al "Biodegradable Polymers Based on Renewable Resources: Polyesters Composed of 1,4 : 3,6-Dianhydrohexitol and Aliphatic Dicarboxylic Acid Units", Journal of Applied Polymer Science, vol. 62, 2257-2265 (1996 (Year: 1996).*
F. Fenouillot et al Polymers from renewable 1,4:3,6-dianhydrohexitols (isosorbide, isomannide and isoidide): A review. Progress in Polymer Science 35 (2010) 578-622. (Year: 2010).*
Richard Norman et al "Chemical Compounds" Encyclopedia Britannica, published Aug. 25, 2022 https://www.britannica.com/science/chemical-compound (Year: 2022).*
Garcia et al., "Polyoxalates from biorenewable diols via Oxalate Methathesis Polymerization", The Royal Society of Chemistry, Polym. Chem, vol. 5, pp. 955-961, 2014.
Rajput et al., "Cross-Methathesis of Biorenewable Dioxalates and Diols to Film-Forming Degradable Polyoxalates", Journal of Polymer Science, Part A: Polymer Chemistry, vol. 56, pp. 1584-1592, 2018.
International Search Report and Written Opinion pertaining to Application No. PCT/IN2018/050457 dated Nov. 21, 2018.

\* cited by examiner

ISOHEXIDE-DIOXALATE COMPOUND, ITS POLYMERS AND APPLICATION THEREOF

FIELD OF THE INVENTION

The present invention relates to an isohexide-dioxalate compound of formula (I). More particularly, the present invention relates to an isohexide-dioxalates compound of formula (I), a process for preparation and use thereof. The present invention further relates to a polyoxalates compound of formula (II), a process for preparation and use thereof.

BACKGROUND AND PRIOR ART OF THE INVENTION

Current situation of polymer industries is strongly dependent on monomers derived from non-renewable fossil feed-stock's. Due to depleting fossil feed-stock's and consequent increasing crude oil prices the scientific community is forced to find better alternatives. Therefore, use of renewable feed-stock could be the one of the better alternatives. Among the various renewable feedstock materials sugars, and plant oils can provide direct entry to chemical modification and functionalization. Along these lines, the renewable resource based products such as poly-lactic acid (PLA), polyhydroxy-alkanoates (PHA) and sugar cane based polyethylene have been recently commercialized. It is appeared that the use of abundant renewable resources such as starch, cellulose and plant oil to develop new chemicals and polymeric materials seems to be a sustainable solution. For instance, sugars can be easily converted to a host of new building blocks and it has naturally inbuilt chirality so it can be creatively utilized to manufacturing of value added chiral reagents. This sugar can be readily converted to bifunctional molecules called isohexides. The beauty of this isohexides is that they are chiral, non-toxic and rigid. Due to this rigid of backbone, incorporation of isohexides in the polymer main-chain will increase the glass transition temperature of resulting polymers. The term isohexides (1,4:3,6-Dianhydrohexitols) refers to sugar derived diols, which consist of three major isomers namely, 1,4:3,6-Dianhydro-D-glucitol (isosorbide, 1a), 1,4:3,6-Dianhydro-D-mannitol (isomannide, 1b) and 1,4:3,6-Dianhydro-L-iditol (isoidide, 1c). The common C6-sugars such as glucose and mannose that are derived from the maize, wheat and potatoes or cereal-based polysaccharides, can be hydrogenated to produce sorbitol and mannitol respectively. Further, double dehydration of sorbitol and mannitol end up with corresponding isosorbide and isomannide.

Among these isohexides the difference is only configuration of the two hydroxyl group located at C2 and C5 position to the bicyclic ether ring. In case of isomannide the configuration of —OH group at C2 and C5 position is endo-endo, whereas in case of isosorbide is endo-exo and in isoidide is exo-exo. Due to this difference in orientation of free hydroxyl groups, isohexides differ physical and chemical properties of the isomers, such as melting temperatures and reactivity of the hydroxyl groups. The endo hydroxyl groups form intramolecular hydrogen bonds to the oxygen atoms of the opposite furan ring, whereas the exo hydroxyl groups are not involved in intramolecular hydrogen bonding. Considering the steric effects and hydrogen bonding, isomannide with two endohydroxyl groups is the least reactive compound compared with isoidide which has two exohydroxyl groups and should be more attractive for biochemical applications. Isoidide shows a significantly higher reactivity, but unfortunately its precursor, L-idose, cannot be obtained from plant biomass asit is rare in nature. The current approach to obtain isoidide goes via inversion of chiral centres of isomannide. Easily accessible isomer such as isosorbide has attracted significant attention, because of orientation of the two hydroxyl group at C2 is exo and that at C5 is endo, due to which isosorbide is more reactive isomer compared to isomannide. Direct utilization of these isohexides in polymerization end up with dark tar like polymer, which could be due to the limited reactivity of secondary —OH group and hydrogen bonding between —OH groups and ether ring oxygen.

Article titled "Polyoxalates from biorenewable diols via Oxalate Metathesis Polymerization" by John J. Garcia et al. published in Polymer Chemistry, 2014, 5, 955-961 reports a method to prepare polyoxalates via an intermediate which was proposed to be a mono-oxalate. However, neither mono-oxalate nor di-oxalate was isolated. Furthermore, existence of such mono-oxalate or di-oxalate species was not proved. The prior art does not mention any application such as film, fibers and composites etc. The prior art uses partly renewable and partly fossil fuel derived monomers such as aromatic monomers.

The direct utilization of isohexides in polymerization leads to dark tar like materials. Apart from renewable origin, degradability is another material requirement for sustainable future.

Therefore, there is need to develop a synthetic strategy that can provide direct access to dioxalates monomers derived from renewable resources such as sugars and plant oils. Such monomers, if made accessible, can be used to obtain renewable polymers. If the resultant polymers are degradable, the approach will be a fully sustainable approach from cradle to grave. Thus, to satisfy the sustainability criteria, an approach that makes use of renewable resources, yields materials that can meet societal demand and degrades in environment without any adverse effect, will be highly desirable. Accordingly, the present invention provides the synthesis of novel class of renewable isohexide-dioxalates and their polymerization with diols to afford polyoxalates.

OBJECTIVES OF THE INVENTION

The main objective of the present invention is to provide an isohexide-dioxalates compound of formula (I) and a process for preparation thereof.

Another objective of the present invention is to provide a polyoxalates compound of formula (II) and a process for preparation thereof.

SUMMARY OF THE INVENTION

Accordingly, the present invention provides an isohexide-dioxalates compound of formula (I);

Formula (I)

wherein
R is selected from the group consisting of $C_1$ to $C_5$ alkyl and $C_1$ to $C_5$ aliphatic chain with heteroatoms.

In a preferred embodiment, the isohexide-dioxalates compound of formula (I) is selected from the group consisting of (O,O'-((3R,6R)-hexahydrofuro[3,2-b]furan-3,6-diyl) dimethyl dioxalate [isomannide-dioxalate], (O,O'-((3R,6S)-hexahydrofuro[3,2-b]furan-3,6-diyl) dimethyl dioxalate [isosorbide-dioxalate] and (O,O'-((3S,6S)-hexahydrofuro[3,2-b]furan-3,6-diyl) dimethyl dioxalate [isoidide-dioxalate].

The isohexide-dioxalate compound of formula (I) is used as a crystallizing agent and as a monomer for synthesis of polyoxalates.

In yet another embodiment, the present invention provides a process for the preparation of the isohexide-dioxalates compound of formula (I) comprising the steps of:
a) adding n-BuLi to a solution of an isohexide in a solvent at temperature in the range of −78° C. to 40° C. to obtain a first reaction mixture and stirring the first reaction mixture at a temperature in the range of 25° C. to 30° C. for the period in the range of 1 to 2 hours to obtain a reaction solution;
b) adding an alkyl chlorooxoacetate to the reaction solution of step (a) at temperature in the range of 0° C. to 5° C. to obtain a second reaction mixture and stirring the second reaction mixture at temperature in the range of 25° C. to 30° C. for the period in the range of 44 to 50 hours to obtain isohexide-dioxalates compound of formula (I).

In still another embodiment, the present invention provides a polyoxalates compound of formula (II);

Formula (II)

wherein
n is selected from 1 to 23;
x is selected from 1-1000;
y is selected from 1-2000;
z is selected from 10 to 1000;
R is selected from the group consisting of $C_1$ to $C_5$ alkyl and $C_1$ to $C_5$ aliphatic chain with heteroatoms.

In yet still another embodiment, the present invention provides a process for the preparation of polyoxalates compound of formula (II) comprising adding a catalyst to a mixture of an isohexide-dioxalates of formula (I), a diol to obtain a reaction mixture and heating the reaction mixture at temperature in the range of 120° C. or 150° C. for the period in the range 1 to 3 hrs and stirring the heated reaction mixture at a temperature of 150° C. for a period in the range of 6 to 96 hours to obtain polyoxalates compound of formula (II).

BRIEF DESCRIPTION OF THE DRAWINGS

FIG. 1. Solution casting of P2(2a-3b) to obtain a transparent film with CSIR-NCL logo in the background.
FIG. 2: Stress-strain curve of P2(2a-3b).
FIG. 3. Storage and loss modulus of P2(2a-3b).
FIG. 4: GPC chromatogram of P1 (2a-3a) in chloroform at room temperature 30° C.
FIG. 5: GPC chromatogram of P2 (2a-3b) in chloroform at room temperature 30° C.
FIG. 6: GPC chromatogram of P3 (2a-3c) in chloroform at room temperature 30° C.
FIG. 7: GPC chromatogram of P4 (2b-3a) in chloroform at room temperature 30° C.
FIG. 8: GPC chromatogram of P5 (2b-3b) in chloroform at room temperature 30° C.
FIG. 9: GPC chromatogram of P6 (2b-3c) in chloroform at room temperature 30° C.

DETAILED DESCRIPTION OF THE INVENTION

Figure 10:
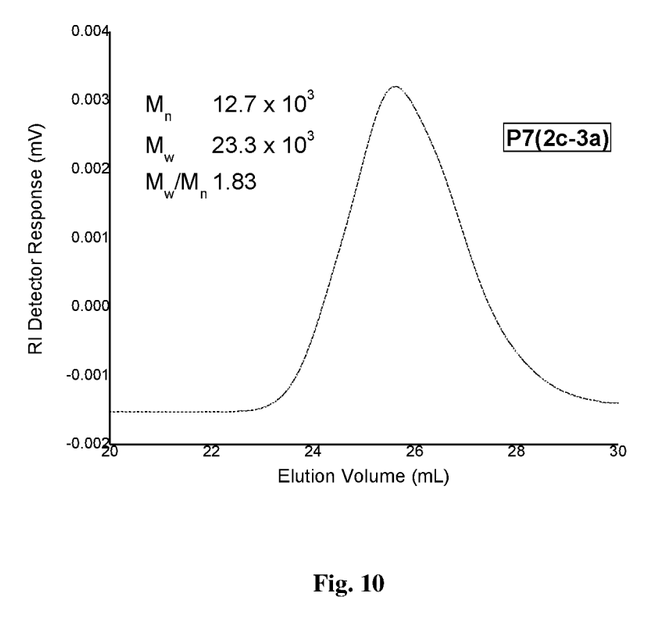
FIG. 10: GPC chromatogram of P7 (2c-3a) in chloroform at room temperature 30° C.
Figure 11:
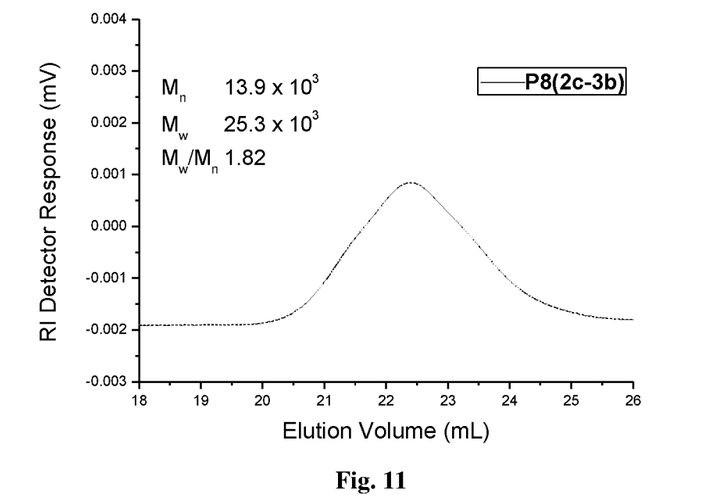
FIG. 11: GPC chromatogram of P8 (2c-3b) in chloroform at room temperature 30° C.
Figure 12:
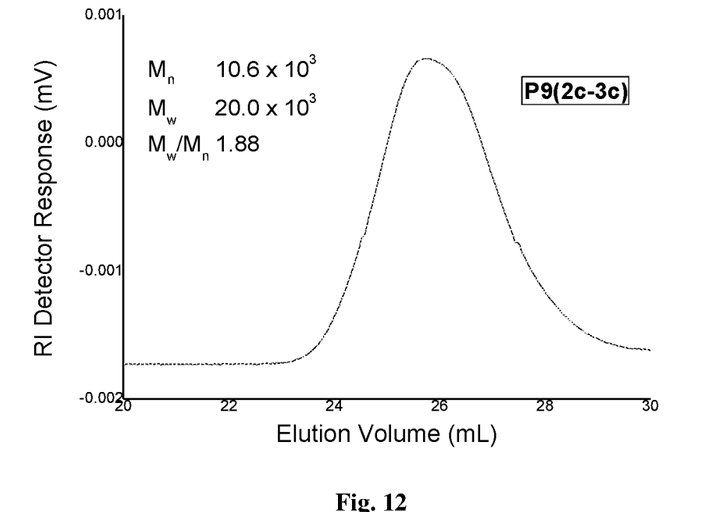
FIG. 12: GPC chromatogram of P9 (2c-3c) in chloroform at room temperature 30° C.

The invention will now be described in detail in connection with certain preferred and optional embodiments, so that various aspects thereof may be more fully understood and appreciated.

The present invention provides an isohexide-dioxalates compound of formula (I), a process for preparation and use thereof. The present invention further relates to a polyoxalates compound of formula (II), a process for preparation and use thereof.

In an embodiment, the present invention provides an isohexide-dioxalates compound of formula (I);

Formula (I)

wherein
R is selected from the group consisting of $C_1$ to $C_5$ alkyl and $C_1$ to $C_5$ aliphatic chain with heteroatoms.

The isohexide-dioxalates compound of formula (I) is selected from the group consisting of (O,O'-((3R,6R)-hexahydrofuro[3,2-b]furan-3,6-diyl) dimethyl dioxalate [isomannide-dioxalate], (O,O'-((3R,6S)-hexahydrofuro[3,2-b]furan-3,6-diyl) dimethyl dioxalate[isosorbide-dioxalate] and (O,O'-((3S,6S)-hexahydrofuro[3,2-b]furan-3,6-diyl) dimethyl dioxalate[isoidide-dioxalate].

The isohexide-dioxalate compound of formula (I) is used as a crystallizing agent and as a monomer for the synthesis of polyoxalates.

In yet another embodiment, the present invention provides a process for the preparation of the isohexide-dioxalates compound of formula (I) comprising the steps of:
a) adding n-BuLi to a solution of an isohexide in a solvent at temperature in the range of −78° C. to 40° C. to obtain a first reaction mixture and stirring the first reaction mixture at a temperature in the range of 25° C. to 30° C. for the period in the range of 1 to 2 hours to obtain a reaction solution;
b) adding an alkyl chlorooxoacetate to the reaction solution of step (a) at temperature in the range of 0° C. to 5° C. to obtain a second reaction mixture and stirring the second reaction mixture at temperature in the range of 25° C. to 30° C. for the period in the range of 44-50 hours to obtain isohexide-dioxalates compound of formula (I).

The isohexide is selected from the group consisting of isomannide, isosorbide and isoidide.

The solvent is selected from the group consisting of tetrahydrofuran (THF), diethyl ether, toluene, dimethoxy ether, and dioxane or combination thereof.

The alkyl chlorooxoacetate is selected from the group consisting of methyl chlorooxoacetate, ethyl chlorooxoacetate, oxalic acid monoethyl ester and ethyl glyoxalate.

The process for the preparation of the isohexide-dioxalates is as depicted in scheme 1:

Scheme 1 Preparation of isohexide-dioxalates.

i) n-BuLi, -78° C., 1 h and 1 h at RT; ii) CH₃OCOCOCl, RT, 48 h.

The attempts to prepare polyoxalates using isohexides and dimethyl oxalates in the presence of an acid catalyst such as p-toluenesulfonic acid end up in dark tar like material (Scheme 2). The limited reactivity of isohexide is due to the sterically encumbered secondary hydroxyl groups. To improve the reactivity, isohexides are functionalized with methyl chlorooxoacetate to make AA type monomers (i.e. isohexide-dioxalates) (Scheme 2). This isohexide-dioxalates is subjected to polymerization with diols in presence of titanium isopropoxide to give the corresponding polyoxalates (Scheme 2).

Scheme 2 Classical method (top) and our approach (bottom) for acylating terminal hydroxyl groups to dioxalate and subsequent polymerization with diols to corresponding polyoxalates.

In still another embodiment, the present invention provides a polyoxalates compound of formula (II);

Formula (II)

wherein
- n is selected from 1 to 23;
- x is selected from 1-1000;
- y is selected from 1-2000;
- z is selected from 10 to 1000;
- R is selected from the group consisting of $C_1$ to $C_5$ alkyl and $C_1$ to $C_5$ aliphatic chain with heteroatoms.

The polyoxalates compound of formula (II) is represented by

Poly(Hexyl (6-(2-oxo-2-(((3R,6R)-6-(2-oxoacetoxy)hexahydrofuro[3,2-b]furan-3-yl)oxy)acetoxy)hexyl)) oxalate [P1(2a-3a)], Poly(Octyl (8-(2-oxo-2-(((3R,6R)-6-(2-oxoacetoxy)hexahydrofuro[3,2-b]furan-3-yl)oxy)acetoxy)octyl)) oxalate [P2 (2a-3b)], Poly(Dodecyl (12-(2-oxo-2-(((3R,6R)-6-(2-oxoacetoxy) hexahydrofuro[3,2-b]furan-3-yl)oxy)acetoxy)dodecyl)) oxalate [P3(2a-3c)], Poly(Hexyl (6-(2-oxo-2-(((3S,6R)-6-(2-oxoacetoxy)hexahydrofuro[3,2-b]furan-3-yl)oxy)acetoxy)hexyl)) oxalate [P4(2b-3a)], Poly(Octyl(8-(2-oxo-2-(((3S,6R)-6-(2-oxoacetoxy)hexahydrofuro[3,2-b]furan-3-yl)oxy)acetoxy)octyl)) oxalate [P5 (2b-3b)], Poly(Dodecyl (12-(2-oxo-2-(((3S,6R)-6-(2-oxoacetoxy) hexahydrofuro[3,2-b]furan-3-yl)oxy)acetoxy)dodecyl)) oxalate [P6(2b-3c)], Poly(Hexyl (6-(2-oxo-2-(((3S,6S)-6-(2-oxoacetoxy)hexahydrofuro[3,2-b]furan-3-yl)oxy)acetoxy)hexyl)) oxalate [P7 (2c-3a)], Poly(Octyl (8-(2-oxo-2-(((3S,6S)-6-(2-oxoacetoxy)hexahydrofuro[3,2-b]furan-3-yl)oxy)acetoxy)octyl)) oxalate [P8 (2c-3b)], and Poly(Dodecyl (12-(2-oxo-2-(((3S,6S)-6-(2-oxoacetoxy) hexahydrofuro[3,2-b]furan-3-yl)oxy)acetoxy)dodecyl)) oxalate [P9(2c-3c)].

The molecular weight of the polyoxalates compound of formula (II) is in the range of 2000 to 220000 g/mol.

In yet still another embodiment, the present invention provides a process for the preparation of polyoxalates compound of formula (II) comprising adding a catalyst to a mixture of an isohexide-dioxalates of formula (I), a diol to obtain a reaction mixture and heating the reaction mixture at temperature in the range of 120° C. or 150° C. for the period in the range 1 to 3 hrs and stirring the heated reaction mixture at a temperature of 150° C. for a period in the range of 6 to 96 hours to obtain polyoxalates compound of formula (II).

The catalyst is selected from the group consisting of p-Toluenesulfonic acid, methane sulfonic acid, trifluoromethane sulfonic acid, titanium methoxide, titanium ethoxide, titanium isopropoxide and titanium tert-butaoxide.

The isohexide-dioxalates compound of formula (I) is selected from the group consisting of (O,O'-((3R,6R)-hexahydrofuro[3,2-b]furan-3,6-diyl) dimethyl dioxalate [isomannide-dioxalate], (O,O'-((3R,6S)-hexahydrofuro[3,2-b]furan-3,6-diyl) dimethyl dioxalate[isosorbide-dioxalate] and (O,O'-((3S,6S)-hexahydrofuro[3,2-b]furan-3,6-diyl) dimethyl dioxalate[isoidide-dioxalate].

The diol is selected from the group consisting of hexane-1,6-diol (3a), octane-1,8-diol (3b), dodecane-1,12-diol (3c), decane-1,10-diol, nonadecane-1,19-diol and tricosane-1,23-diol.

The reaction is carried out under argon atmosphere.

The polyoxalates compound of formula (II) is used for the preparation of films and fibers, composites and fibers.

The process for the synthesis of polyoxalates from isohexide-dioxalates and diols is as depicted in scheme 3:

bide backbone) and 4.2 ppm ("F" protons from the long-chain aliphatic segment). The 4.2 ppm "F" protons further displayed cross peaks to methylene carbons (G and H) in the range of 25-29 ppm. Thus, the above NMR experiments unambiguously prove the existence of anticipated polyoxalate and demonstrate through bond correlation between "D-E-E-F" type protons and carbons. Polymerization conditions like time, temperature and catalyst loading are optimized to get the highest molecular weight polymer and which is monitored by GPC.

The gel permeation chromatography (GPC) investigation of the polyoxalates P1(2a-3a)-P9(2c-3c) revealed a molecular weight in the range of 14000-68000 g/mol (Run 1-9, The polyoxalates of formula (II) are characterized using a combination of spectroscopic and analytical methods. The formation of high molecular weight polyoxalate P1(2a-3a)-P9(2c-3c) is confirmed by the reduced intensity of a proton resonance at around 3.89-3.91 although these signals overlap with backbone signals and absence of a $^{13}C$ peak at 53 ppm (corresponding to terminal —$OCH_3$ group). The ratio of eight backbone protons of 2b (1:3:1:1:2) is retained in P5(2b-3b). The splitting pattern of the polymer backbone protons is similar to that of 2b protons; suggesting that the stereochemistry of the monomer 2b is most likely preserved during the polymerization. These typical features are associated with all other polyoxalates derived from isomannide and isoidide.

In a decisive long-range through bond C—H correlation experiment (HMBC), an oxalate carbon ("E" carbon) at around 157-158 ppm revealed through bond correlation to protons at 5.3 ("D" proton that originates from the isosortable 1) which is achieved using 1 mol % of catalyst and polymerization time is 48 hours. Thermal properties of polyoxalate are determined by differential scanning colorimetry (DSC). Polyoxalates derived from long chain diols displayed higher melting temperature compared to their shorter chain analogue (Table 1).

TABLE 1

Polyoxalates derived from the renewable feedstocks and their properties [a]

| Run | Monomers | Polymers | Mol. Wt $(10^3)$[b] g/mol | PDI[b] | Tm (° C.)[c] |
|---|---|---|---|---|---|
| 1 | 2a-3a | P1(2a-3a) | 40.6 | 2.00 | NO |
| 2[d] | 2a-3b | P2(2a-3b) | 68.2 | 2.20 | 45 |
| 3[e] | 2a-3c | P3(2a-3c) | 41.6 | 1.81 | 63 |
| 4 | 2b-3a | P4(2b-3a) | 14.5 | 2.05 | NO |

TABLE 1-continued

Polyoxalates derived from the renewable feedstocks and their properties [a]

| Run | Monomers | Polymers | Mol. Wt (10³)[b] g/mol | PDI[b] | Tm (° C.)[c] |
|---|---|---|---|---|---|
| 5[f] | 2b-3b | P5(2b-3b) | 31.9 | 1.94 | 44 |
| 6[g] | 2b-3c | P6(2b-3c) | 23.4 | 2.16 | 50 |
| 7[h] | 2c-3a | P7(2c-3a) | 23.3 | 1.83 | NO |
| 8[d] | 2c-3b | P8(2c-3b) | 25.3 | 1.82 | 46 |
| 9[h] | 2c-3c | P9(2c-3c) | 20.0 | 1.88 | 54 |

[a] Conditions: 2a-b: 3.14 mmol, 3a-c.: 3.14 mmol, Ti(OiPr)₄: 0.0314 mmol (1 mol %), Temp.: 120-150° C., Time: 48 h, Yields are listed in Table 2.
[b] Mol. wt. and polydispersity index (PDI) were obtained from GPC in chloroform with respect to polystyrene standards.
[c] Obtained from DSC measurements.
[d] 2a/2c and 3b = 2.61 mmol.
[e] 2a and 3c = 2.47 mmol.
[f] 2b and 3b = 2.02 mmol.
[g] 2b and 3c = 2.68 mmol.
[h] 2c and 3a/3c = 2.83 mmol.
NO = could not be observed The highest molecular weight polyoxalates P2(2a-3b) (Run-2, table 1) are tested for making film by solution casting. Mechanical properties of as prepared film are measured on Dynamic Mechanical Analyzer (DMA). There is minimum molecular weight requirement to form an entanglement networked structure of chains. It is also known that strength and elongation increases with increased molecular weight. This is due to increased entanglements of chains with increased molecular weight. In case of long entangled chains, it requires higher stress to get fully extended. Low molecular weight polymer contains less entangled short chains which easily can be slipped upon applying stress. The formation of films (FIG. 1) prove that synthesized polymer has enough molecular weight with chain entanglements to form a network structure.

Due to increased molecular weight there is more number of chains possibilities to form a highly intertwined chain network. The intertwined network of long chains makes it more resistant to respond for a mechanical stress. Stress and strain at break behavior as shown in (FIG. 2) and table 2 summarizes the most significant data.

TABLE 2

Strain and stress at break of P2(2a-3b).

| Stress (in MPa) | 3.25 |
|---|---|
| % Strain | 23% |

After having established the reactivity, polymerization conditions are optimized and Table 1 summarizes the most significant results.

The present invention also provides a synthesis of renewable feedstock chemicals with a degradable oxalate group incorporated into the building block. The synthetic utility of these feedstock chemicals is demonstrated by preparing corresponding film forming, high molecular weight, degradable, polyoxalates via an intriguing dioxalate-diol cross metathesis polymerization reaction.

Following examples are given by way of illustration therefore should not be construed to limit the scope of the invention.

EXAMPLES

Example 1: Synthesis of Isomannide-Dioxalate (2a)

To a stirred solution of isomannide (0.516 g, 3.53 mmol in 20 ml dry THF) was slowly added the n-BuLi (4.1 ml, 8.12 mmol) at −78° C. and the mixture stirred for 1 hour. After that, the resulting mixture is stirred at room temperature (30° C.) for over a period of 1 hour. To this mixture was added methyl chlorooxoacetate (0.74 ml, 8.12 mmol) at 0° C. and it was further stirred for next 48 hours at room temperature (30° C.). The reaction mixture was washed with saturated sodium chloride solution (20 ml) and the aqueous phase was extracted with ethyl acetate (3×20 ml). The combined organic phase was dried over MgSO₄, filtered and the filtrate was evaporated in vacuum to obtain a highly viscous material. Purification by column chromatography (pet ether-ethyl acetate 55:45) resulted in highly viscous liquid. To this residue ethyl acetate was added and white solid was formed after addition of excess pet ether to ethylene acetate solution. The white solid was isolated after evaporation of solvents yielding 0.94 g of the desired isomannide-dioxalate (84%) as a white solid.

¹H NMR (400 MHz, CDCl₃, 298 K) δ=5.20-5.16 (m, 2H$_D$), 4.80-4.79 (m, 2H$_C$), 4.08-3.97 (m, 4H$_B$), 3.89 (s, 6H$_A$); ¹³C NMR (100 MHz, CDCl₃, 298 K) δ=157.6-156.9 (s, C$_B$), 80.1 (s, C$_C$), 75.7 (s, C$_D$), 70.3 (s, C$_B$), 53.8 (s, C$_A$). ESI-MS (+ve mode) m/z=341.04 [M+Na]⁺; Elemental analysis (%) calculated for C₁₂H₁₄O₁₀: C—45.29%, H—4.43%; Found: C—45.97%, H—4.23%.

Example 2: Synthesis of Isosorbide-Dioxalate (2b)

To a stirred solution of isosorbide (0.516 g, 3.53 mmol in 20 ml dry THF) was slowly added n-BuLi (4.1 ml, 8.12 mmol) at −78° C. and the mixture is stirred for 1 hour. After that resulting mixture is stirred at room temperature (30° C.) for additional 1 hour. To this mixture was added methyl chlorooxoacetate (0.74 ml, 8.12 mmol) at 0° C. and the reaction was stirred for next 48 hours at room temperature (30° C.). Subsequently, the reaction mixture was washed with saturated sodium chloride solution (20 ml) and the aqueous phase was extracted with ethyl acetate (3×20 ml). The combined organic phase was dried over MgSO$_4$, filtered and the filtrate was evaporated in vacuum to obtain a highly viscous material. Purification by column chromatography (pet ether-ethyl acetate 55:45) obtained highly viscous liquid. This residue was dissolved in ethyl acetates and was precipitated as a white solid after addition of excess pet ether. The white solid was isolated after evaporation of solvents yielding 0.85 g of the desired isosorbide-dioxalate (2b) (76%) as a white solid.

$^1$H NMR (400 MHz, CDCl$_3$, 298 K) δ=5.33-5.30 (m, 2H$_D$), 5.01-4.98 (m, 1H$_C$), 4.59-4.58 (m, 1H$_C$), 4.08-3.94 (m, 4H$_B$), 3.91-3.89 (s, 6H$_A$); $^{13}$C NMR (100 MHz, CDCl$_3$, 298 K) δ=157.7-156.8 (s, C$_B$), 85.8 (s, C$_C$), 80.9 (s, C$_C$), 80.3 (s, C$_D$), 76.2 (s, C$_D$), 73.1 (s, C$_B$), 70.8 (s, C$_B$), 53.9 (s, C$_A$). ESI-MS (+ve mode) m/z=341.04 [M+Na]$^+$; Elemental analysis (%) calculated for C$_{12}$H$_{14}$O$_{10}$: C—45.29%, H—4.43%; Found: C—45.90%, H—4.33%.

Example 3: Synthesis of Isoidide-Dioxalate (2c)

To a stirred solution of isoidide (0.516 g, 3.53 mmol in 20 ml dry THF) was slowly added the n-BuLi (4.1 ml, 8.12 mmol) at −78° C. and the mixture was stirred for 1 hour. Next, the Schlenk tube was brought to room temperature (30° C.) and was stirred for an additional hour. Then, methyl chlorooxoacetate (0.74 ml, 8.12 mmol) was added at 0° C. and further stirred for next 48 hours at room temperature (30° C.). The reaction mixture was washed with saturated sodium chloride solution (20 ml) and the aqueous phase was extracted with ethyl acetate (3×20 ml). The combined organic phase was dried over MgSO$_4$, filtered and the filtrate was evaporated in vacuum to obtain a highly viscous material. Purification by column chromatography (pet ether-ethyl acetate 55:45) yielded a highly viscous liquid. This residue was dissolved in ethyl acetate and was precipitated by adding excess pet ether to produce white solid. The white solid was isolated after evaporation of solvents yielding 0.60 g of the desired isoidide-dioxalate (2c) (53%).

$^1$H NMR (400 MHz, CDCl$_3$, 298 K) δ=5.33 (m, 2H$_D$), 4.79 (m, 2H$_C$), 4.02 (m, 4H$_B$), 3.88 (s, 6H$_A$); $^{13}$C NMR (100 MHz, CDCl$_3$, 298 K) δ=157.2-156.3 (s, C$_B$), 84.8 (s, C$_C$), 79.5 (s, C$_D$), 71.9 (s, C$_B$), 53.6 (s, C$_A$). ESI-MS (+ve mode) m/z=319.06 [M+H]$^+$; Elemental analysis (%) calculated for C$_{12}$H$_{14}$O$_{10}$: C—45.29%, H—4.43%; Found: C—45.15%, H—3.87%.

Example 4: Polymerization of Isohexide-Dioxalate (2a-c) and Diols (3a-c) to Polyoxalates P1 (2a-3a)-P9(2c-3c)

The polyoxalates were prepared in a 50 ml Schlenk tube equipped with an overhead mechanical stirrer, heating arrangement and vacuum-purge system. Isohexide-dioxalates (2a-c) and linear-diols (3a-c) were transferred to the schlenk tube and the catalyst (1 mol %) of titanium isopropoxide was added under positive argon flow. The monomers (neat monomers) were melted by heating and polymerization was started at 120° C. Next, over a period of 2 hours the temperature was raised to 150° C. with intermittent vacuum after every 3-5 minutes to knock-off the byproduct (methanol). Finally, the polymer melt was stirred for next 46 hours under reduced pressure (0.01 mbar). The thus obtained polymer was dissolved in chloroform and precipitated by pouring in methanol (around 100 ml). The resultant polymers were isolated in semi-solid material which was dried in vacuum. The quantitative details of various polyoxalates are summarized in table 3. Synthesized polyoxalates were characterized and representative NMR data were provided in following section.

TABLE 3

Polymerization of isohexide-dioxalates (2a-c) and linear-diols (3a-c)

| Run | Polyoxalates | 2a-c g(mmol) | 3a-c g(mmol) | Ti(OiPr)$_4$ (mmol) | Theoretical yield (g) | Isolated yield (g) | Yield (%) |
|---|---|---|---|---|---|---|---|
| 1 | P1(2a-3a) | 1.0 (3.14) | 0.37 (3.14) | 0.0314 | 1.17 | 0.73 | 62 |
| 2 | P2(2a-3b) | 0.83 (2.61) | 0.38 (2.61) | 0.0261 | 1.05 | 0.60 | 57 |
| 3 | P3(2a-3c) | 0.78 (2.47) | 0.50 (2.47) | 0.0247 | 1.13 | 0.77 | 68 |
| 4 | P4(2b-3a) | 1.0 (3.14) | 0.37 (3.14) | 0.0314 | 1.17 | 0.84 | 72 |
| 5 | P5(2b-3b) | 0.64 (2.02) | 0.29 (2.02) | 0.0202 | 0.81 | 0.50 | 62 |
| 6 | P6(2b-3c) | 0.85 (2.68) | 0.54 (2.68) | 0.0268 | 1.22 | 0.91 | 74 |
| 7 | P7(2c-3a) | 0.9 (2.83) | 0.33 (2.83) | 0.0283 | 1.05 | 0.69 | 65 |
| 8 | P8(2c-3b) | 0.83 (2.61) | 0.38 (2.61) | 0.0261 | 1.05 | 0.68 | 65 |
| 9 | P9(2c-3c) | 0.9 (2.83) | 0.57 (2.83) | 0.0283 | 1.29 | 0.95 | 74 |

Example 5: NMR Data of Polyoxalates a) P1(2a-3a):

$^1$H NMR (500 MHz, CDCl$_3$, 298K) δ=5.18 (br., 2H$_D$), 4.80 (br., s, 2H$_C$), 4.26 (br., s, 8H$_F$), 4.07-3.98 (br., s, 4H$_B$), 1.74 (br., s, 8H$_G$), 1.42 (br., s, 8H$_H$). $^{13}$C NMR (125 MHz, CDCl$_3$, 298K) δ=157.9-156.4 (m, C$_E$), 79.9 (s, C$_C$), 75.6 (s, C$_D$), 70.2 (s, C$_B$), 67.1-66.8 (m, C$_F$), 28.1 (s, C$_G$), 25.3 (s, C$_H$).

b) P2(2a-3b):

$^1$H NMR (400 MHz, CDCl$_3$, 298K) δ=5.19 (br., 2H$_D$), 4.81 (br., s, 2H$_C$), 4.27 (br., s, 12H$_F$), 4.06 (br., s, 4H$_B$), 1.73 (br., s, 12H$_G$), 1.36 (br., s, 23H$_H$). $^{13}$C NMR (100 MHz, CDCl$_3$, 298K) δ=157.9-157.0 (m, C$_E$), 79.8 (s, C$_C$), 75.4 (s, C$_D$), 70.0 (s, C$_B$), 66.9 (m, C$_F$), 28.8 (s, C$_G$), 28.1-25.4 (s, C$_H$).

c) P3(2a-3c):

$^1$H NMR (400 MHz, CDCl$_3$, 298K) δ=5.18 (br., 2H$_D$), 4.81 (br., s, 2H$_C$), 4.26 (br., s, 8H$_F$), 4.07-4.00 (br., s, 4H$_B$), 1.72 (br., s, 9H$_G$), 1.26 (br., s, 34H$_H$). $^{13}$C NMR (100 MHz, CDCl$_3$, 298K) δ=157.9-157.1 (m, C$_E$), 79.9 (s, C$_C$), 75.5 (s, C$_D$), 70.1 (s, C$_B$), 67.4-67.1 (m, C$_F$), 29.4 (s, C$_G$), 29.4, 29.1, 28.2, 25.6 (s, C$_H$).

d) P4(2b-3a):

$^1$H NMR (400 MHz, CDCl$_3$, 298K) δ=5.31 (br., 2H$_D$), 4.98 (br., s, 1H$_C$), 4.58 (br., s, 1H$_C$), 4.26 (br., s, 6H$_F$), 4.05 (br., s, 3H$_B$), 3.92 (br., s, 1H$_B$), 1.74 (br., s, 6H$_G$), 1.42 (br., s, 6H$_H$). $^{13}$C NMR (100 MHz, CDCl$_3$, 298K) δ=157.9-156.9 (m, C$_E$), 85.7 (s, C$_C$), 80.8 (s, C$_C$), 80.1 (s, C$_D$), 76.0 (s, C$_D$), 72.9 (s, C$_B$), 70.7 (s, C$_B$), 67.1-66.8 (m, C$_F$), 28.1 (s, C$_G$), 25.3 (s, C$_H$).

e) P5(2b-3b):

$^1$H NMR (500 MHz, CDCl$_3$, 298K) δ=5.30 (br., 2H$_D$), 4.97 (br., s, 1H$_C$), 4.56 (br., s, 1H$_C$), 4.24 (br., s, 8H$_F$), 4.04 (br., s, 3H$_B$), 3.91-3.89 (br., s, 1H$_B$), 1.70 (br., s, 8H$_G$), 1.32 (br., s, 16H$_H$). $^{13}$C NMR (125 MHz, CDCl$_3$, 298K) δ=158.0-157.0 (m, C$_E$), 85.7 (s, C$_C$), 80.8 (s, C$_C$), 80.0 (s, C$_D$), 75.9 (s, C$_D$), 72.8 (s, C$_B$), 70.7 (s, C$_B$), 67.3-67.0 (m, C$_F$), 28.9 (s, C$_G$), 25.6 (s, C$_H$).

f) P6(2b-3c):

¹H NMR (400 MHz, CDCl₃, 298K) δ=5.32 (br., 2H$_D$), 4.99 (br., s, 1H$_C$), 4.59 (br., s, 1H$_D$), 4.27 (br., s, 6H$_F$), 4.06 (br., s, 4H$_B$), 1.72 (br., s, 7H$_G$), 1.28 (br., s, 25H$_H$). ¹³C NMR (100 MHz, CDCl₃, 298K) δ=158.0-157.0 (m, C$_E$), 85.7 (s, C$_C$), 80.7 (s, C$_C$), 80.0 (s, C$_D$), 76.2-75.9 (s, C$_D$), 72.8 (s, C$_B$), 70.7 (s, C$_B$), 67.5-67.1 (m, C$_F$), 29.4 (s, C$_G$), 29.1-25.6 (s, C$_H$).

g) P7(2c-3a):

¹H NMR (400 MHz, CDCl₃, 298K) δ=5.31 (br., 2H$_D$), 4.78 (br., s, 2H$_C$), 4.26 (br., s, 8H$_F$), 4.02 (br., s, 4H$_B$), 1.73 (br., s, 7H$_G$), 1.42 (br., s, 7H$_H$). ¹³C NMR (100 MHz, CDCl₃, 298K) δ=157.9-156.8 (m, C$_E$), 85.0 (s, C$_C$), 80.0-79.7 (m, C$_D$), 72.1 (s, C$_B$), 67.1-66.8 (m, C$_F$), 28.1 (s, C$_G$), 25.3 (s, C$_H$).

h) P8(2c-3b):

¹H NMR (500 MHz, CDCl₃, 298K) δ=5.32 (br., 2H$_D$), 4.79 (br., s, 2H$_C$), 4.25 (br., s, 7H$_F$), 4.02 (br., s, 4H$_B$), 3.86 (br., 1H$_A$), 1.71 (br., s, 7H$_G$), 1.33 (br., s, 15H$_H$). ¹³C NMR (125 MHz, CDCl₃, 298K) δ=158.0-156.8 (m, C$_E$), 85.1-85.0 (m, C$_C$), 79.7 (s, C$_D$), 72.1-72.0 (m, C$_B$), 67.4-67.0 (m, C$_F$), 28.9 (s, C$_G$), 28.2 (s, C$_H$), 25.6 (s, C$_H$).

i) P9(2c-3c):

$^1$H NMR (500 MHz, CDCl$_3$, 298K) δ=5.33 (br., 2H$_D$), 4.80 (br., s, 2H$_C$), 4.27 (br., s, 7H$_F$), 4.04 (br., s, 4H$_B$), 1.72 (br., s, 8H$_G$), 1.28 (br., s, 27H$_H$). $^{13}$C NMR (125 MHz, CDCl$_3$, 298K) δ=158.1-156.9 (m, C$_E$), 85.2 (s, C$_C$), 80.1-79.7 (m, C$_D$), 72.2 (s, C$_B$), 67.6-67.2 (m, C$_F$), 29.5 (s, C$_G$), 29.2-25.7 (m, C$_D$).

Example 6: Film Preparation of Polyoxalate P2(2a-3b) by Solution Casting A 10 wt % polymer solution was prepared in chloroform (3 ml). Homogeneous polymer solution was poured in Teflon petri dish and was air dried in fume hood for 72 hours. The resultant film was sticky in nature and therefore it was further dried in a vacuum oven at 50° C. for another 48 h to remove any residual solvent present. Film was peeled off gently from Teflon petri dish and used as it is for mechanical characterization.

Advantages of the Invention

1) Use of sugar and plant oil derived molecules.
2) A single step synthetic protocol to prepare renewable isohexide-dioxalates.
3) Novel isohexide-dioxalates are chiral compounds and can be used in many organic transformations.
4) High molecular weight polyoxalates have been prepared.
5) The resultant polyoxalates can be drawn into transparent films.

We claim:
1. A polyoxalate polymer having formula (II);

Formula (II)

wherein
n is from 1 to 23;
x is from 1 to 1000;
y is from 1 to 2000;
z is from 10 to 1000; and
R is selected from the group consisting of C$_1$ to C$_5$ alkyl and C$_1$ to C$_5$ aliphatic chain with heteroatoms; and
wherein the polyoxalate polymer of formula (II) has a weight average molecular weight of from 2000 g/mol to 220000 g/mol.

2. The polyoxalate polymer of formula (II) according to claim 1, wherein said polyoxalate polymer is selected from group consisting of
Poly(Hexyl(6-(2-oxo-2-(((3R,6R)-6-(2-oxoacetoxy) hexahydrofuro[3,2-b]furan-3-yl)oxy)acetoxy)hexyl)) oxalate,
Poly(Octyl(8-(2-oxo-2-(((3R,6R)-6-(2-oxoacetoxy)hexahydrofuro[3,2-b]furan-3-yl)oxy)acetoxy)octyl)) oxalate,
Poly(Dodecyl (12-(2-oxo-2-(((3R,6R)-6-(2-oxoacetoxy) hexahydrofuro[3,2-b]furan-3-yl)oxy)acetoxy)dodecyl)) oxalate,
Poly(Hexyl(6-(2-oxo-2-(((3S,6R)-6-(2-oxoacetoxy)hexahydrofuro[3,2-b]furan-3-yl)oxy)acetoxy)hexyl)) oxalate,
Poly(Octyl(8-(2-oxo-2-(((3S,6R)-6-(2-oxoacetoxy)hexahydrofuro[3,2-b]furan-3-yl)oxy)acetoxy)octyl)) oxalate,
Poly(Dodecyl (12-(2-oxo-2-(((3S,6R)-6-(2-oxoacetoxy) hexahydrofuro[3,2-b]furan-3-yl)oxy)acetoxy)dodecyl)) oxalate,
Poly(Hexyl(6-(2-oxo-2-(((3S,6S)-6-(2-oxoacetoxy)hexahydrofuro[3,2-b]furan-3-yl)oxy)acetoxy)hexyl)) oxalate,
Poly(Octyl(8-(2-oxo-2-(((3S,6S)-6-(2-oxoacetoxy)hexahydrofuro[3,2-b]furan-3-yl)oxy)acetoxy)octyl)) oxalate, and
Poly(Dodecyl (12-(2-oxo-2-(((3S,6S)-6-(2-oxoacetoxy) hexahydrofuro[3,2-b]furan-3-yl)oxy)acetoxy)dodecyl)) oxalate.

3. A process for preparing the polyoxalate polymer according to claim 1, said process comprising:
(i) adding a catalyst to a mixture of an isohexide-dioxalate of formula (I):

Formula (I)

where R is selected from the group consisting of C$_1$ to C$_5$ alkyl and C$_1$ to C$_5$ aliphatic chain with heteroatoms, and a diol to obtain a reaction mixture, and heating the reaction mixture at temperature from 120° ° C. to 150° C. for from 1 hour to 3 hours; and
(ii) stirring the heated reaction mixture at a temperature of 150° ° C. for from 6 hours to 96 hours to obtain the polyoxalate compound of formula (II).

4. The process according to claim 3, wherein said catalyst is selected from the group consisting of p-toluenesulfonic acid, methane sulfonic acid, trifluoromethane sulfonic acid, titanium methoxide, titanium ethoxide, titanium isopropoxide, and titanium tert-butoxide; and wherein said diol is selected from the group consisting of hexane-1,6-diol, octane-1,8-diol, dodecane-1,12-diol, decane-1,10-diol, nonadecane-1,19-diol, and tricosane-1,23-diol.

5. The process according to claim 3, wherein said isohexide-dioxalate compound of formula (I) is selected from the group consisting of
(O,O'-((3R,6R)-hexahydrofuro[3,2-b]furan-3,6-diyl) dimethyl dioxalate,
(O,O'-((3R,6S)-hexahydrofuro[3,2-b]furan-3,6-diyl) dimethyl dioxalate and
(O,O'-((3S,6S)-hexahydrofuro[3,2-b]furan-3,6-diyl) dimethyl dioxalate.

6. The process according to claim 3, wherein said catalyst is selected from the group consisting of p-toluenesulfonic acid, methane sulfonic acid, trifluoromethane sulfonic acid, titanium methoxide, titanium ethoxide, titanium isopropoxide, and titanium tert-butoxide.

7. The process according to claim 3, wherein said diol is selected from the group consisting of hexane-1,6-diol, octane-1,8-diol, dodecane-1,12-diol, decane-1,10-diol, nonadecane-1,19-diol, and tricosane-1,23-diol.

8. The process according to claim 3, further comprising, before (i) and (ii), preparing the isohexide-dioxalate compound of formula (I) by:
    (a) adding n-BuLi to a solution of an isohexide in a solvent at temperature from −78° C. to 40° ° C. to obtain a first reaction mixture and stirring the first reaction mixture at a temperature from 25° ° C. to 30° C. for from 1 hour to 2 hours to obtain a reaction solution; and
    (b) adding an alkyl chlorooxoacetate to the reaction solution of (a) at temperature from 0° ° C. to 5° ° C. to obtain a second reaction mixture and stirring the second reaction mixture at temperature from 25° ° C. to 30° ° C. for from 44 hours to 50 hours to obtain isohexide-dioxalate compound of formula (I).

9. The process according to claim 8, wherein the isohexide of (a) is selected from the group consisting of isomannide, isosorbide, and isoidide.

10. The process according to claim 8, wherein the solvent of (a) is selected from the group consisting of tetrahydrofuran, diethyl ether, toluene, dimethoxy ether, dioxane, and combinations thereof.

11. The process according to claim 8, wherein the alkyl chlorooxoacetate of (b) is selected from the group consisting of methyl chlorooxoacetate, ethyl chlorooxoacetate, oxalic acid monoethyl ester, and ethyl glyoxalate.

12. The process according to claim 8, wherein:
    the isohexide of (a) is selected from the group consisting of isomannide, isosorbide, and isoidide:
    the solvent of (a) is selected from the group consisting of tetrahydrofuran, diethyl ether, toluene, dimethoxy ether, dioxane, and combinations thereof; and
    the alkyl chlorooxoacetate of (b) is selected from the group consisting of methyl chlorooxoacetate, ethyl chlorooxoacetate, oxalic acid monoethyl ester, and ethyl glyoxalate.

* * * * *